United States Patent [19]

Arad et al.

[11] Patent Number: 5,534,417
[45] Date of Patent: Jul. 9, 1996

[54] MICROORGANISM GROWTH APPARATUS

[75] Inventors: Shoshana (Malis) Arad, Omer; Ephraim Cohen, Lehavim, both of Israel

[73] Assignee: Ben-Gurion University of the Negev, Beer-Sheva, Israel

[21] Appl. No.: 337,737

[22] Filed: Nov. 14, 1994

Related U.S. Application Data

[62] Division of Ser. No. 332,437, Oct. 31, 1994, which is a continuation of Ser. No. 69,347, May 28, 1993, abandoned.

[30] Foreign Application Priority Data

Jun. 12, 1992 [IL] Israel ......................................... 102189

[51] Int. Cl.$^6$ .............................. C12P 23/00; C12N 1/12; C12M 1/04
[52] U.S. Cl. ...................... 435/67; 435/257.1; 435/292.1
[58] Field of Search .................................... 435/42, 257.1, 435/257.2, 67, 257.3, 257.4, 946, 284, 286, 296, 311, 313–316, 813, 819, 292.1, 296.1, 295.2; 47/1.4, 1.401, 1.402, 1.406, 1.409

[56] References Cited

U.S. PATENT DOCUMENTS

| 2,371,208 | 3/1945 | Alzola . |
| 2,686,754 | 8/1954 | Monod . |
| 2,732,663 | 1/1956 | Dewey . |
| 3,102,082 | 8/1963 | Brewer . |
| 3,186,917 | 6/1965 | Gerhardt et al. . |
| 3,955,317 | 5/1976 | Gudin . |
| 4,519,984 | 5/1985 | Hitzman . |
| 4,868,123 | 9/1989 | Berson et al. . |

FOREIGN PATENT DOCUMENTS

| 0343885 | 11/1989 | European Pat. Off. | 435/313 |
| 2202549 | 9/1988 | United Kingdom | 435/284 |
| 9105849 | 5/1991 | WIPO | 435/284 |

*Primary Examiner*—William H. Beisner
*Attorney, Agent, or Firm*—Kane, Dalsimer, Sullivan, Kurucz, Levy, Eisele and Richard

[57] ABSTRACT

A method of growing microalgae is described, which uses the outdoor sunlight as a source of energy. Growth is confined to an assembly of vertical, transparent tubes through which nutrient and air is carried with carbon dioxide. The microalgae is periodically harvested from the tubes.

22 Claims, 7 Drawing Sheets

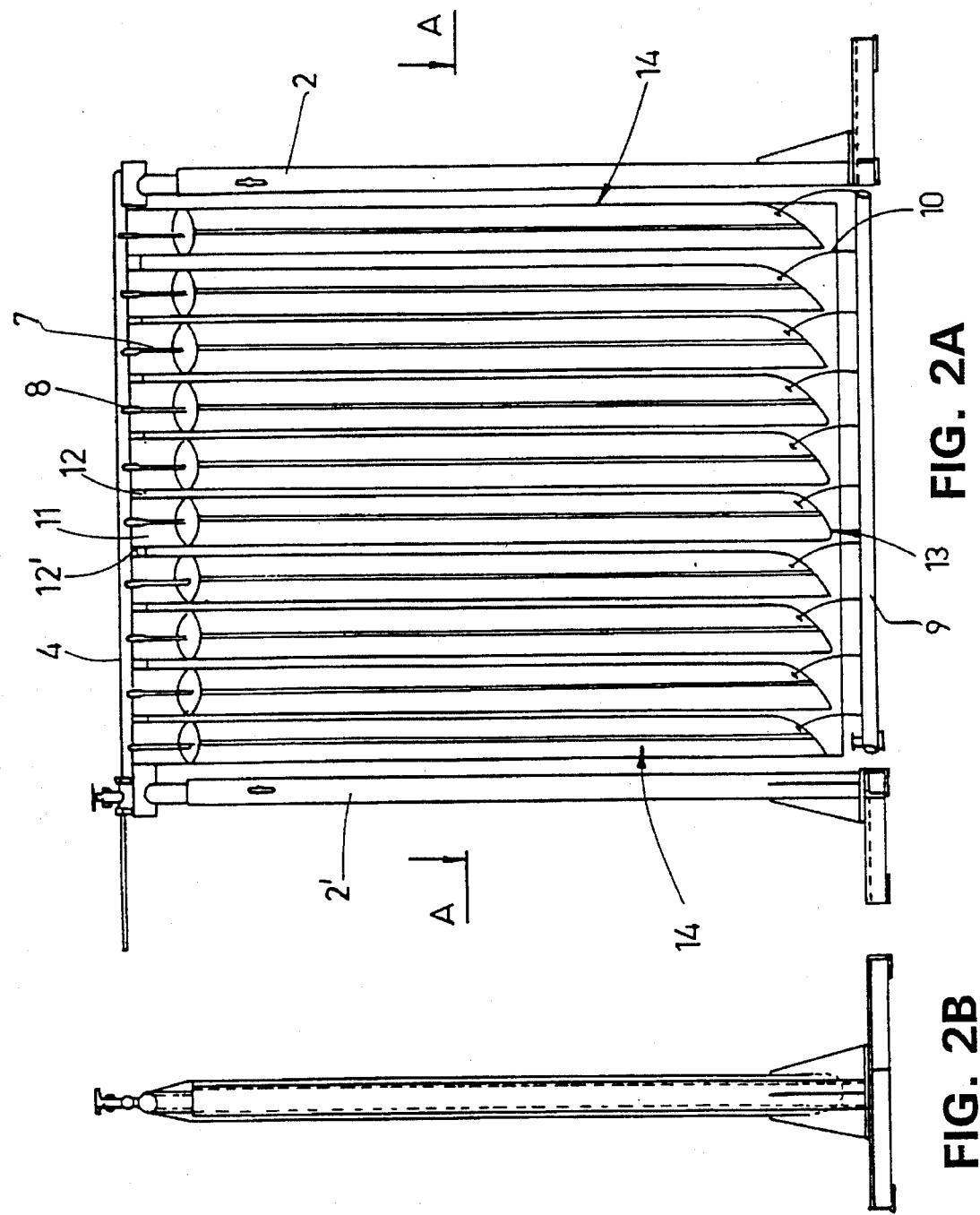

MICROORGANISM GROWTH APPARATUS

CROSS REFERENCE TO RELATED APPLICATIONS

This is a Division of copending application Ser. No. 08/332,437 filed Oct. 31, 1994 which is a Continuation of U.S. application Ser. No. 08/069,347 filed May 28, 1993, now abandoned.

FIELD OF THE INVENTION

The present invention relates to an apparatus for growing microorganisms, particularly algae. More particularly, the invention relates to apparatus for the outdoor production of microorganisms on an industrial scale.

BACKGROUND OF THE INVENTION

Growth of microorganisms outdoors is effected in a number of cases where lighting has a beneficial effect on the growth of such microorganisms. Microorganisms commonly grown outdoors are microalgae, and for the purpose of simplicity, throughout the specification reference will be made to microalgae, it being understood that this does not imply a limitation of the apparatus of the invention for growing other species, including such species which do not require light conditions for growing. Illustrative microorganisms which can be grown according to the present invention include, fungi, yeast, bacteria, macroalgae, plant cells and nematodes.

THE PRIOR ART

Microalgae are normally grown outdoors in ponds, whenever it is desired to produce industrial amounts of biomass, thus exploiting sunlight for such growth. It has also been attempted to grow microalgae outdoors in apparatus including transparent tubings, although apparatus of various kinds, such as those disclosed in U.S. Pat. Nos. 2,732,663, 3,955, 317 and 4,868,123, has generally not met with technological and commercial success on an industrial scale.

The above methods, however, suffer from severe drawbacks. Production in ponds is non-efficient and suffers from problems deriving from poor light penetration, temperature fluctuations during the day and contamination with hostile microorganisms, accumulation of oxygen, and evaporation which results in salination. Growth in transparent tubings and pipes has been suggested, but all known growing methods have the considerable drawback of being non-efficient, and particularly of not being applicable on an industrial scale because of low yield and high apparatus costs.

SUMMARY OF THE INVENTION

It is an object of the present invention to provide apparatus for growing microorganisms, particularly microalgae, outdoors, in high yield, in industrial amounts and at relatively low costs.

The microorganism-growth apparatus according to the invention comprises in combination:

a) a plurality of vertical elongated transparent flexible cells, capable of containing a biomass;

b) vertical support means to support the said plurality of cells in close juxtaposition to one another, and in vertical position;

c) at least one gas inlet and one gas outlet, to permit the bubbling of nutrient or other gas through the biomass and the ventilation of each cell;

d) at least one inlet and/or outlet to permit feeding of nutrient solution to the biomass and harvesting of the biomass from each cell; and e) common conveying means connected to each of the said outlets, to receive and convey biomass harvested from the said plurality of cells, all or part of them, away from the growth apparatus.

Thus, according to the invention, and as will be explained hereinafter, it is possible to grow large amounts of biomass in apparatus which occupies a relatively small area, because of the high yield in vertical growth.

According to a preferred embodiment of the invention, the vertical support means comprise a vertical frame, having at least two vertical elements and one upper horizontal element, the said upper horizontal element being adapted to support the weight of the said plurality of cells.

In order to be able to combine the said plurality of cells with the frame, the cells are provided with connecting means which are connectable to the horizontal element of the vertical frame, whereby the said plurality of cells, when connected to the said horizontal element, hang therefrom.

According to one preferred embodiment of the invention each two adjacent cells are connected at at least one point, and preferably the are all interconnected. This can be achieved in various ways. E.g., openings can be left in the welding between two adjacent cells, so that mass can pass from one cell to the other, or external connecting means can be provided, e.g., at the extremity of the cell, which can be used to connect all cells to common connecting means through which, e.g., it is possible to empty the cells, fully or partially, at the same time or alternately, as dictated by the particular requirements of the system. this, as will be appreciated, allows for considerably flexibility of operation, which is another advantage of the invention.

As stated, one of the objects of the invention is to provide efficient apparatus to produce biomass in high yields, while utilizing a relatively small space. This is important, because in order to produce biomass in industrial quantities, the configuration of the apparatus must be adapted to a production of given amounts of biomass per square meter, and should not be below certain minimal values. In microalgae production a biomass growth of 25 g/m$^2$·day is recognized in the art as an upper limit for industrial manufacturing. However, practical yields of microalgae growth in ponds do not normally exceed 2.5–10 g/m$^2$/day.

In a preferred embodiment of the invention, the distance between two adjacent cells is 100 mm or less. This is important not only for the purpose of increasing the yield of the apparatus, but also in order to avoid or minimize interference between adjacent cells, as far as light penetration is concerned.

The apparatus of the invention also permits to obtain higher and more desirable temperatures during winter months, as well as to avoid too high temperatures in summer months, while exploiting excellent light conditions.

Production of microalgae in the apparatus of the invention has also the substantial advantage of permitting the precipitation of the microalga during harvesting, without the need for pH control. In comparison, in apparatus according to the prior art it is necessary to control the pH in the alga-containing nutrient solution, prior to the precipitation of the algal body, e.g., in a suitable conical collector, because otherwise imperfect or no precipitation takes place and biomass is carried away from the precipitation area by the nutrient solution. For instance, while harvesting *Dunaliella sp.*, which is an important alga for biomass production, it is necessary to reduce the pH of the biomass from its normal value of 7.0–7.5 to about pH 5.5, in order to obtain precipitation. In contrast, when *Dunaliella sp.* is grown in an apparatus according to the invention, precipitation takes place at the same pH in which growth takes place, e.g., pH 7.0–7.5. The reasons for this unexpected behavior, which is also a part of the present invention, are not fully clear. While not wishing to be bound by any specific theory, the inventors believe that the reason for this behavior may be the increased cell concentration per volume, or the increased production of various materials, such as β-carotene, by the algae when they are grown according to the invention, as compared with conventional methods. In any case, this behavior permits to recycle the nutrient solution to the growth apparatus, immediately after precipitation of the biomass, without any treatment or pH adjustment.

Because no mechanical processing is involved (e.g., centrifugation), no substantial breakage of cells occurs and, therefore, the nutrient solution is not contaminated with organic materials such as glycerol or β-carotene, and therefore it can be directly recycled. As will be apparent to the skilled person, this is a considerable processual and economic advantage over prior art processes, because while nutrient solution recycle may be relatively non-important when the prior art processes are carried out on a bench scale, it is economically important when industrial production is considered, as is the case according to the present invention.

In one embodiment of the invention, each cell is separately connected to the vertical frame, and the cells are positioned close to one another so as to form a single body. According to a most preferred embodiment of the invention, all cells are connected to form a single body.

The cells are preferably made of weldable material. Accordingly, as will be appreciated by a skilled person, it is possible to assemble an apparatus of the invention in different ways. For instance, a plurality of cells can be singly provided and close to one another, and then adjacent cells can be welded to one another. According to a preferred embodiment of the invention, the plurality of cells are created in a double layer of weldable material, by welding the said two layers vertically at intervals.

While it is not the intention of the inventors to limit the material of which the cells are made, and such cells can be made of any suitable material, as long as it possesses the appropriate mechanical and optical properties, it has been found that polyethylene is a convenient and suitable material, because it can be easily welded, it possesses good transparency to light and is relatively resistant to wear during operation. Other suitable materials to be used together with polyethylene, or in its stead, include, e.g., polyamides and PVC.

In another embodiment of the invention, separate cells can be interconnected by providing connecting means, e.g., tubings or openings, thereby permitting passage and circulation of biomass and/or nutrient solution from one cell to another. This is convenient in certain applications, when it is desired to homogenize conditions in separate cells, as much as possible.

As will be appreciated by a skilled person, the width of a single cell cannot be too small or too great, because inappropriate dimensions will lead to a malfunctioning of the apparatus, would cause difficult circulation and solution and biomass, and will entail different disadvantages. Accordingly, the perimeter of each cell, as defined hereinafter with reference to the drawings, is preferably comprised between 5 cm and 100 cm. Likewise, the height of each cell should be preferably comprised between 100 and 250 cm. As will be apparent to the skilled person, too high a cell may lead to difficulties of operation, while a too short one will unduly limit the possible yield.

The cross-section of each cell (taken on a horizontal plane) may be of different shapes. However, an elliptical shape is generally preferred, both for constructional strength and ease of manufacturing.

All the above and other characteristics and advantages of the invention will be better understood through the following description of preferred embodiments, with reference to the drawings, wherein:

DESCRIPTION OF THE DRAWINGS

FIG. 2 (*b*) is a cross-sectional view of FIG. 2(*a*) and

FIG. 2(*c*) shows a cross-sectional view taken along lines A—A of FIG. 2(*a*).

DETAILED DESCRIPTION OF PREFERRED EMBODIMENTS

Figure 1:
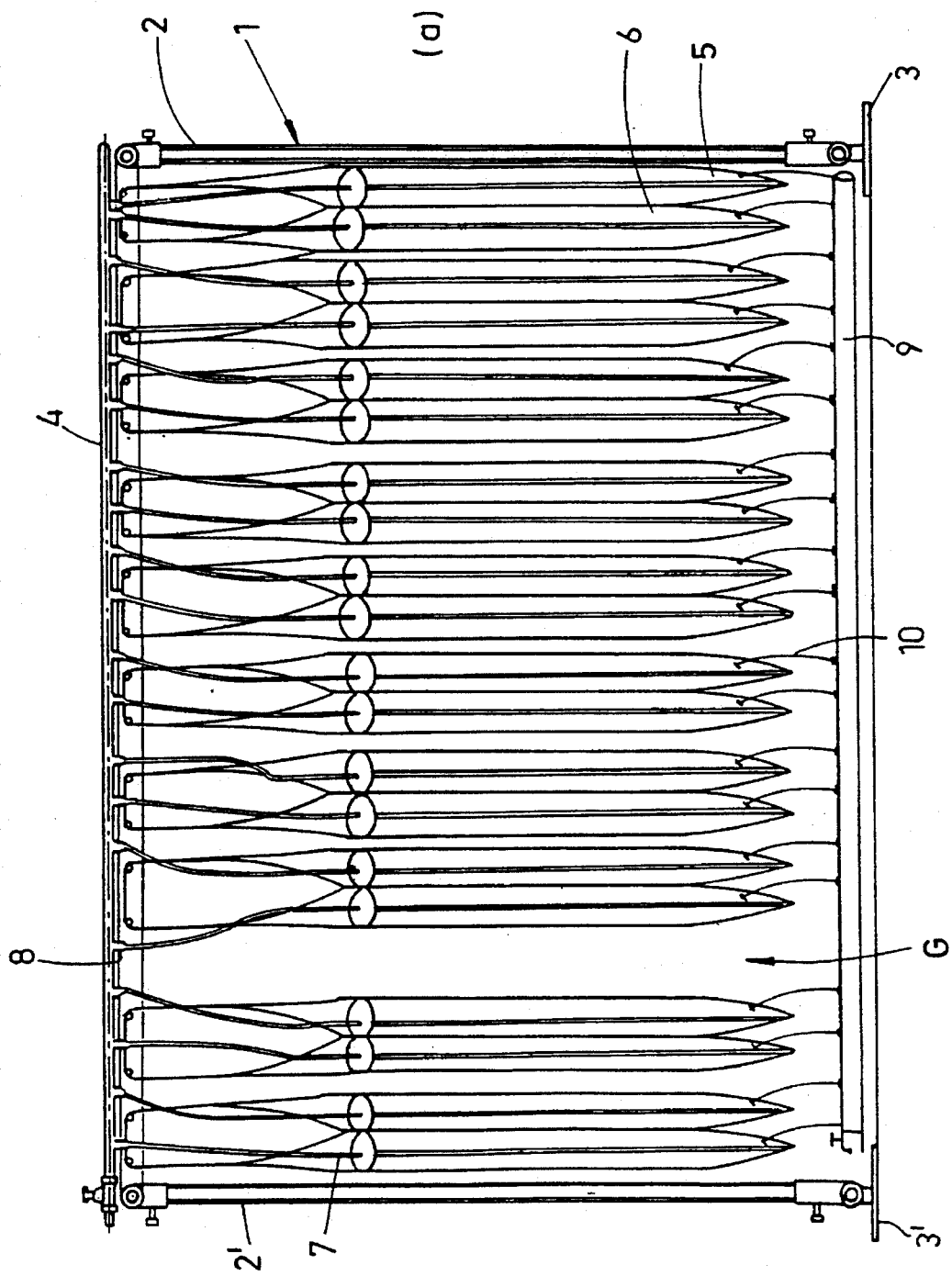
FIG. 1 illustrates an apparatus according to one embodiment of the invention.

Turning now to FIG. 1, the apparatus comprises a vertical frame, generally indicated by numeral 1, having two vertical posts, 2 and 2', which are connected to the ground through bases 3 and 3'. A horizontal element, 4, is used to hang the different cells, and kennels will be used to convey gases to each cell.

The cells shown in this figure are double cells, which comprise two separate cells, 5 and 6, a plurality of such double cells being positioned one near the other so as to form a single compact body. Gap G is shown in the figure only for the sake of illustration, but it is normally not desired to provide such gaps in the apparatus of the invention.

As stated, gas is bubbled into the cells through pipes 7, which originate from a central pipe, which can be positioned within horizontal element 4, as seen in this figure, and which is provided with a plurality of T connections 8. Gas is vented through openings in the cells (not shown).

At the bottom of the apparatus a central pipe 9 is provided, which is connected to pumping elements (not shown), which can be located far away from the apparatus, and which may service a number of similar apparatuses. Filling and harvesting tubing 10 is provided for each cell, through which a biomass is contained in the cell is harvested by pumping through pipe 9, and nutrient solution is refilled by reversing the pumping direction.

Turning now to FIG. 2, this figure illustrates an apparatus according to another preferred embodiment of the invention, all cells being provided in a single body. These cells have been constructed by taking two sheets of polyethylene and welding them so as to leave empty cells between the two sheets. Looking at FIG. 2(a), the cells 11 are seen to be created by the welding lines 12 and 12', which constitutes the borders of the cell. At the bottom welding has been made at an angle, as indicated by arrow 13. The reason for this pointed welding is that it is desirable to provide a pointed end to each cell so that gas introduced by a dip pipe at that location flows up with an increased velocity, thereby aiding fluidization of biomass.

As in the apparatus of FIG. 1, the frame comprises two vertical elements 2 and 2', and a horizontal element 4 from which the set of cells, collectively indicated by 14, hangs. Like before, bubbling of gas (normally air and 2–3% $CO_2$) is effected through a pipe 7, and harvesting and refill of nutrient solution is effected for each cell through tube 10, all tubes 10 being connected to pipe 9, which is in turn connected to pumping means.

It should be understood that, when a plurality of such apparatuses is provided, it is possible to carry out harvesting and refill of nutrient solution by emptying and refilling them one at a time, or a number of them at a time, or all of them together, all according to the capacity of the piping and of the pumping apparatus, but using a plurality of such apparatuses allows for a great flexibility of operation.

Of course, a plurality of apparatuses such as that depicted in FIG. 2 can be assembled in rows or by placing them end to end, to provide an array of such apparatuses. This can also be appreciated by looking at FIG. 2(b), which shows the apparatus as seen from the side.

Figure 2C:
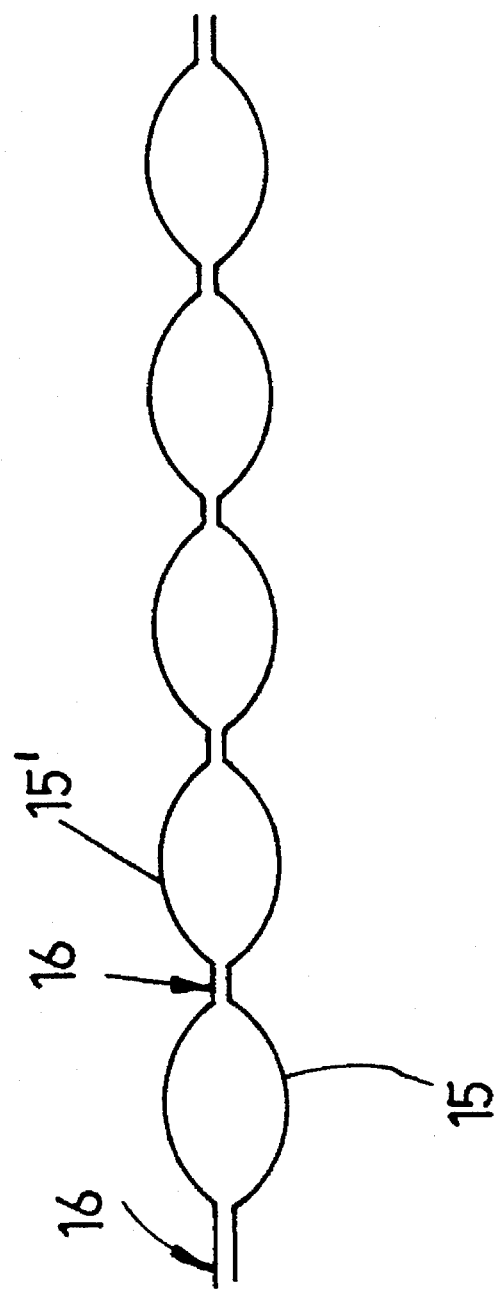
FIG. 2(*a*) is a side view of another preferred embodiment of the invention.
Figure 3:
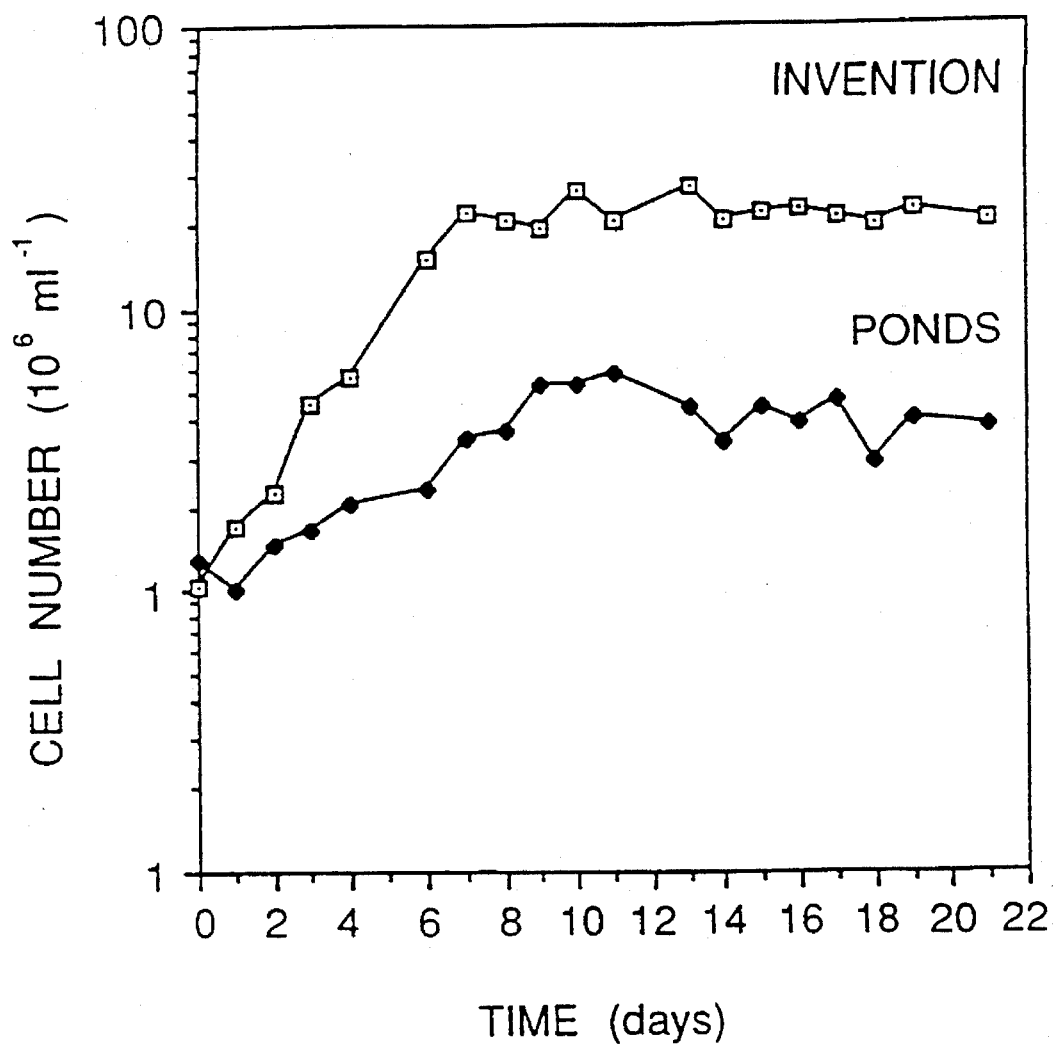
FIG. 3 shows a comparison between growth of *Chlorella emersonii*, grown in ponds, and according to the invention, the comparison being carried out according to cell number.
Figure 4:
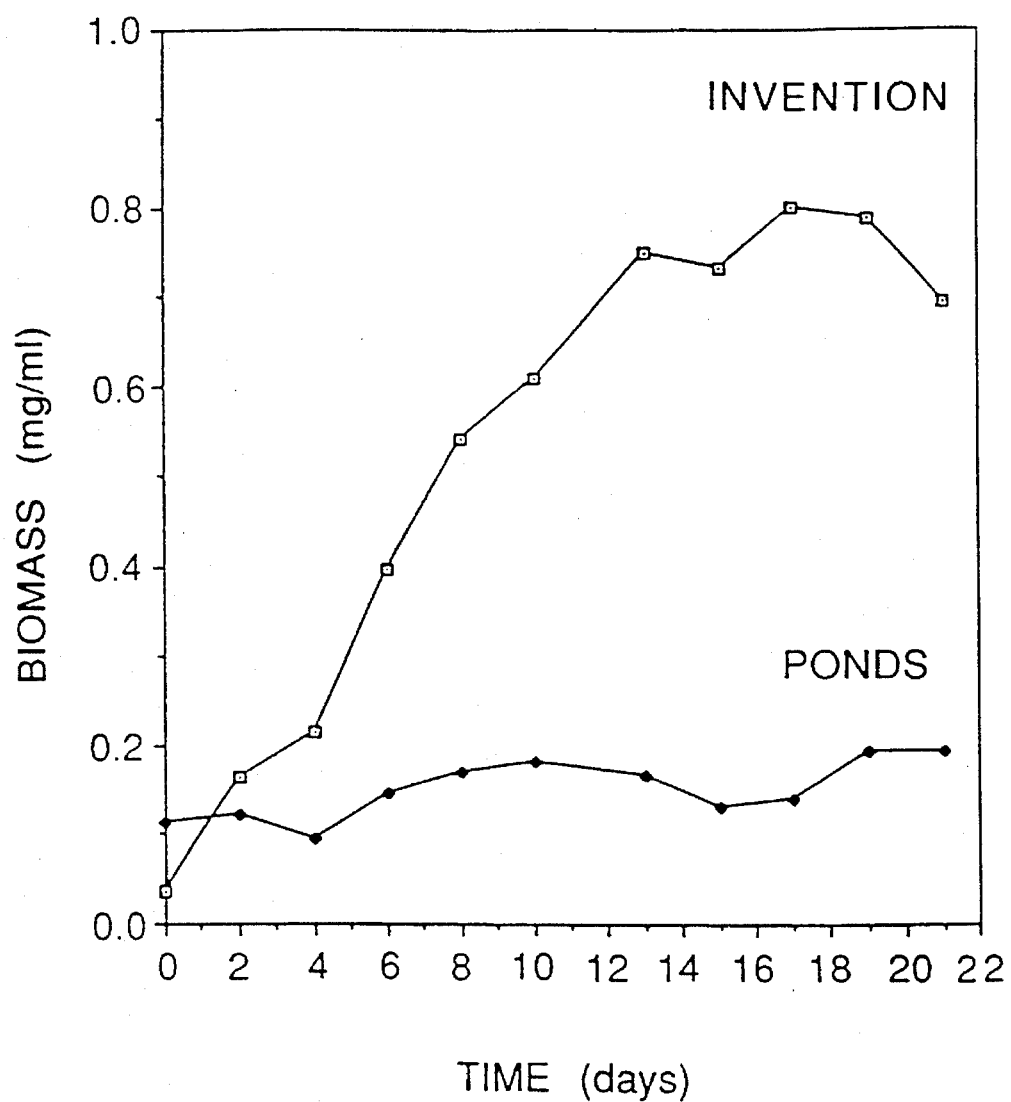
FIG. 4 shows a comparison between biomass of Chlorella in ponds and in an apparatus of the invention.
Figure 5:
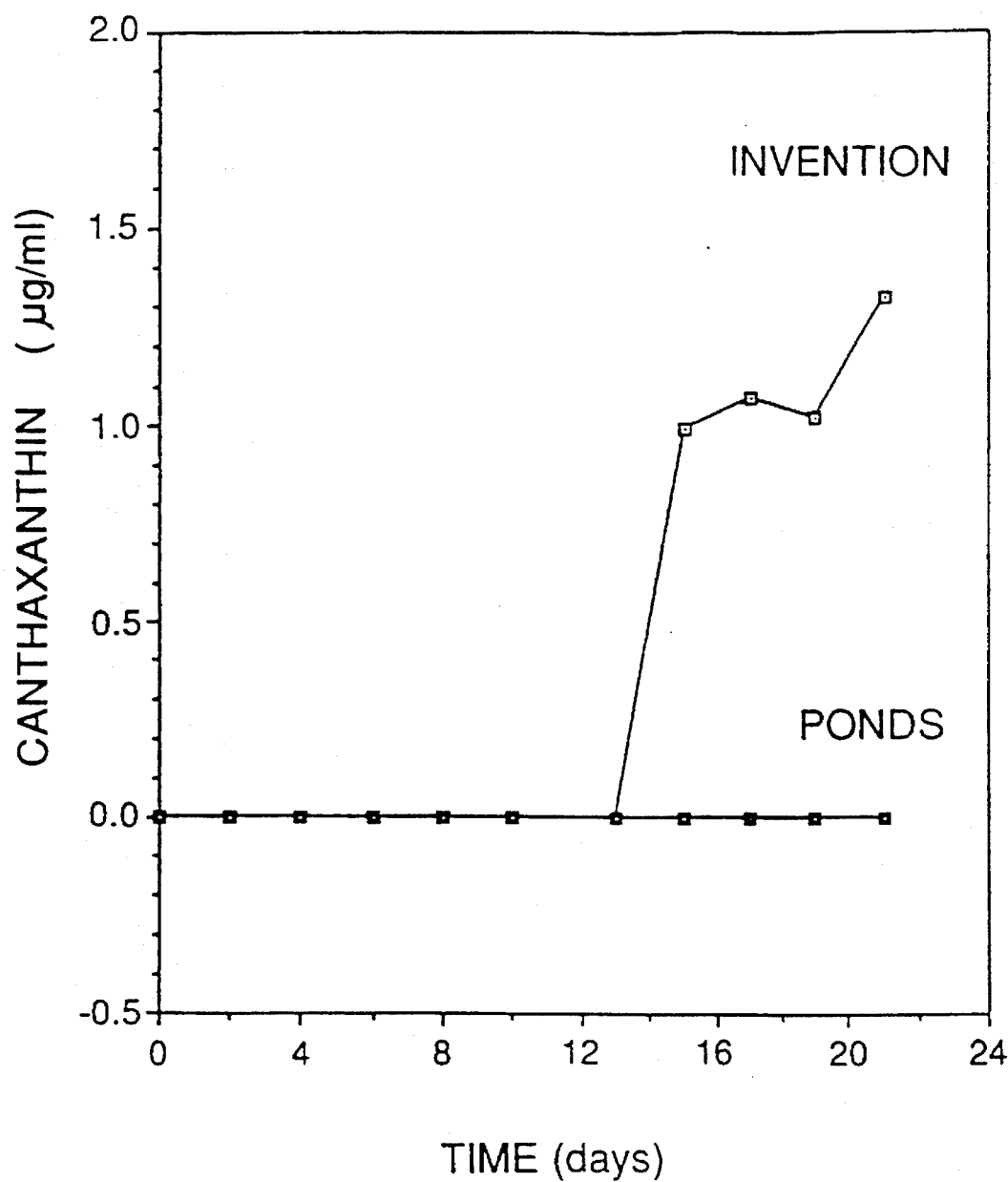
FIG. 5 shows the production of canthaxanthin in ponds and in an apparatus of the invention.
Figure 6:
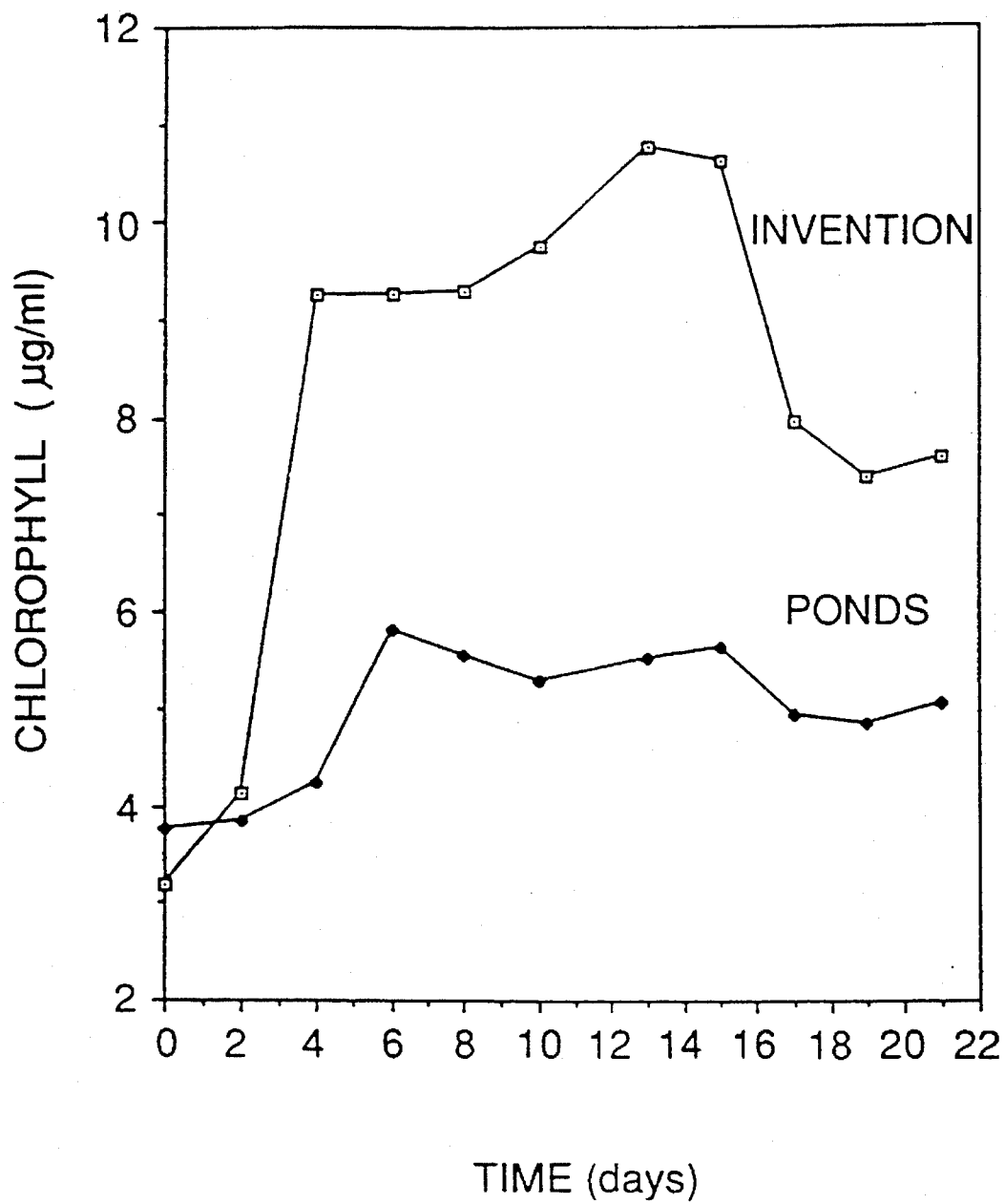
FIG. 6 shows the comparison between the production of chlorophyll in ponds and in an apparatus of the invention.

FIG. 2(c) shows how the cell set 14 of FIG. 2(a) is assembled. This figure, which shows a cross-section taken on the AA plane of FIG. 2(a), distantly shows two sheets of material, indicated by 15 and 15', between which weldings 16 have been effected. The resulting shape is that of a plurality of cells, the distance between which is the distance of the welding.

As stated, it may be desirable to cool the biomass during hot hours, particularly during summertime. This may be achieved in a variety of ways, but a convenient means of cooling comprises sprinkling water along each cell, when the temperature increases. This can be easily done by providing sprinkling means around the top of each cell, which may all be connected through a common water-supply pipe. Sprinkling of water can be effected, e.g., by temperature control through thermocouples inserted in the culture, or by any other suitable means which will be apparent to a skilled person. Wetting of the outer surface of the cell leads to a cooling of the biomass through its evaporation and heat removal from the nutrient solution.

The apparatus of FIG. 2 has been used to run comparative experiments with growth in ponds, as detailed hereinafter.

EXAMPLE 1

An apparatus was built according to the embodiment of FIG. 2, having the following structural characteristics: Perimeter of the horizontal cross-section of each cell: 40 cm. Height-Total: 2.0 m, Full: 1.80 m. Distance between two adjacent cells: 2 cm. In this apparatus there was growth of the green microalga *Chlorella emersonii*, from which a number of materials can be produced. Growth took place outdoors, starting with a biomass of $1 \times 10^6$ cells/ml, using an N-8 nutrient solution, which is identified in Table I below.

The pH of the solution is 6–7.

TABLE I

| Component | Weight (g/lit) in Nutrient Solution |
|---|---|
| $KNO_3$ | 0.1–1.000 |
| $CaCl_2 \times 2H_2O$ | 0.013 |
| $Na_2HPO_4 \times 2H_2O$ | 0.260 |
| $KH_2PO_4$ | 0.740 |
| $MgSO_4 \times 7H_2O$ | 0.050 |
| FeEDTA | 0.010 |
| $Al_2(SO_4)_3 \times 18H_2O$ | $0.035 \times 10^{-4}$ |
| $MnCl_2 \times 4H_2O$ | $0.013 \times 10^{-3}$ |
| $CuSO_4 \times 5H_2O$ | $0.018 \times 10^{-4}$ |
| $ZnSO_4 \times 7H_2O$ | $0.032 \times 10^{-3}$ |
| $CoSO_4 \times 7H_2O$ | $0.018 \times 10^{-4}$ |

The same growth was undertaken in a plurality of ponds having an area of $1 m^2$, a depth of 20 cm, which were mixed with a paddle wheel. Initial conditions and growth conditions were identical in both cases.

A number of parameters were measured as a function of time, the experiments being carried out for twenty-one days. The measured values were cell number, biomass, content of the carotenoid canthaxanthin and of chlorophyll in the microalga. The content of these pigments, as will be apparent to the skilled person, is a measure of the effectiveness of the light processes.

As can be seen by looking at FIGS. 3 through 6, in all cases production in the apparatus of the invention was considerably more effective than the corresponding production in ponds. Only for canthaxanthin the difference became sensible after 12 days.

The parameters measured above illustrate the high effectiveness of the apparatus of the invention.

EXAMPLE 2

The results given above have been given in detail for *Chlorella emersonii*. However, it is clear that the same advantages are present in the growth of other species. This advantage is even more pronounced when, as was the case also in Example 1, the materials which are to be produced by the microorganism, e.g., carotenoids, are produced in concentrations which are dependent on high light availability to the cells. For instance, *Dunaliella bardawill* has been grown in the apparatus of FIG. 2, and such growth has shown equally efficient, and superior as compared with growth in ponds.

The following constructional and operational data were employed in these experiments:

Nutrient Solution

As a nutrient solution there was employed a solution containing the elements detailed in Table II below. The pH of the solution is 7–8.

TABLE II

| Component | Weight (g/lit) in Nutrient Solution |
|---|---|
| NaCl** | 150–250 |
| $NaHCO_3$ | 0.420 |
| $KNO_3$ | 0.03–0.09 |
| $CaCl_2 \times 2H_2O$ | 0.030 |
| $KH_2PO_4$ | 0.272 |
| $MgSO_4 \times 7H_2O$ | 1.240 |
| $MnCl_2 \times 4H_2O$ | $0.400 \times 10^{-3}$ |
| $CuCl_2 \times 2H_2O$ | $0.040 \times 10^{-3}$ |

TABLE II-continued

| Component | Weight (g/lit) in Nutrient Solution |
|---|---|
| $ZnCl_2$ | $0.040 \times 10^{-3}$ |
| $CoCl_2 \times 6H_2O$ | $0.015 \times 10^{-3}$ |
| $H_3BO_3$ | $0.600 \times 10^{-3}$ |
| $(NH_4)_6Mo_7O_{24} \times 4H_2O$ | $0.370 \times 10^{-3}$ |

**Dissolved in tap water.

Growth Apparatus

The apparatus employed was as depicted in FIG. 2, in which the height of each cell was 200 cm (total) and 170 cm (full), and the circumference of each cell was 36 cm, totalling about 18 liters per each cell. Four rows (viz. 4 apparatuses as in FIG. 2) were employed, each comprising 30 cells, with a length of 4 meters, giving a total of 540 lit. per row and of 2160 lit for the entire apparatus. The distance between each row was 2 meters, and the total area occupied by the apparatus was 27.2 sq. meters.

Initiation of Growth

The cells were filled with the nutrient solution through pipes 10 (FIG. 2), which solution contained a concentration of $3 \times 10^5$ cells of *D. bardawill* per ml. solution. The concentration of β-carotene in the solution was 8.6 μg/ml, and of chlorophyll was 1.0 μg/ml.

Harvesting

Harvesting was effected when the monitored concentration of β-carotene in the solution reached a value between 40–60 μg/ml during summertime, and 30–40 μg/ml during wintertime, provided the ratio between the concentrations of β-carotene to chlorophyll was not less than 8. The number of cell per milliliter of culture was $1.5–2 \times 10^6$ during the summer, and $1–1.5 \times 10^6$ during the winter.

Harvesting was effected by withdrawing 50% of the solution to a conical tank through pipe 9 (FIG. 2), and was left to precipitate. After about 12–24 hours precipitation was completed and the upper fraction from the tank was returned to the cells, again via pipes 9. The volume of each cell was made-up with fresh nutrient solution. The biomass deposited from each cell accounted for about 3% of the total volume of the cell.

PERFORMANCE

The performance of the tested apparatus was determined in terms of the amount of β-carotene produced. Two different runs were carried out, one in the winter and one in the summer.

Summer Production

The production test was carried out in the period: Apr. 30, 1991 to Jun. 11, 1991 (a total of 42 days). The results are shown in Table III below.

TABLE III

| Harvest Date (1991) | Conc. of β-carotene in the culture (mg/ml) | Amount of β-carotene Harvested (mg/lit) |
|---|---|---|
| MAY 11 | 81 | 40.5 |
| MAY 20 | 53 | 26.5 |
| MAY 26 | 46 | 23.0 |
| MAY 30 | 42 | 21.0 |
| JUNE 2 | 41 | 20.5 |
| JUNE 6 | 40 | 20.0 |
| JUNE 9 | 41 | 20.5 |
| JUNE 11 | 30 | 15.0 |

A total of 403.92 gr β-carotene were produced during this experiment. The temperature in the culture (maintained by cooling through sprinklers) was 28°–32° C. throughout daytime. The intensity of solar radiation in the area was 2,000–2,500 μE/(m²×sec). The 9 cis:all trans isomer ratio was 60:40.

Winter Production

The production test was carried out in the period: Oct.20, 1991 to Dec.8, 1991 (a total of 50 days). The results are shown in Table IV below.

TABLE IV

| Harvest Date (1991) | Conc. of β-carotene in the culture (mg/ml) | Amount of β-carotene Harvested (mg/lit) |
|---|---|---|
| OCT 26 | 32 | 16 |
| NOV 3 | 36 | 18 |
| NOV 7 | 30 | 15 |
| NOV 11 | 32 | 16 |
| NOV 17 | 36 | 18 |
| NOV 24 | 37 | 18.5 |
| NOV 28 | 27 | 13.5 |
| DEC 8 | 36 | 18 |

A total of 287.28 gr β-carotene were produced during this experiment. The temperature in the culture varied between about 5° C. at 8 AM, to about 20° C. at 4 PM. The intensity of solar radiation in the area was 100–700 μE/(m²×sec). The 9 cis:all trans isomer ratio was 75:25.

All the above has been given for the purpose of illustration, and is not intended to constitute a limitation of the invention. The invention can be exploited for the growth of a large variety of microorganisms, and is not limited to be used with specific biomasses. Furthermore, many different constructions, shapes of cells and frames, construction materials and the like can be provided, all without exceeding the scope of the invention.

We claim:

1. A method of growing microalgae outdoors, comprising the steps of:
   A) providing a growth apparatus located outdoors, comprising in combination:
      a) a plurality of vertical elongated transparent flexible cells, capable of containing a biomass, the plurality of cells being exposed to daylight;
      b) vertical support means to support the plurality of cells in close juxtaposition to one another, and in vertical position;
      c) at least one gas inlet and one gas outlet, to permit the bubbling of gas through the biomass in each cell and the ventilation of each cell;
      d) at least one fluid inlet and/or fluid outlet to permit feeding of nutrient solution to the biomass and harvesting of the biomass from each cell; and e) common conveying means connected to each said at least one fluid inlet and/or fluid outlet for harvesting the biomass, to receive and convey biomass harvested from the plurality of cells, all or part of them, away from the growth apparatus;

B) filling the cells of the provided growth apparatus through said at least one fluid inlet and/or fluid outlet with a nutrient solution containing microalgae to be grown;

C) bubbling through said at least one gas inlet and the growth apparatus cells filled with nutrient solution, air in an amount sufficient to obtain efficient mixing of the biomass and removal of oxygen therefrom through said at least one gas outlet;

D) providing to the growth apparatus cell contained biomass, $CO_2$ in an amount sufficient to promote biomass growth;

E) periodically harvesting from the cells of the growth apparatus the biomass grown by removing a fraction of the volume contained in each cell through said common conveying means, causing solids contained therein to precipitate and recycling the solution from which the solids have precipitated to the cells through said at least one fluid inlet and/or fluid outlet; and F) making-up the fraction removed from the growth apparatus cells with nutrient solution and/or materials as required.

2. A method according to claim 1, wherein the vertical support means of the apparatus comprise a vertical frame, having at least two vertical elements and one upper horizontal element, the said upper horizontal element being adapted to support the weight of the said plurality of cells.

3. A method according to claim 2, wherein the plurality of cells are provided with connecting means, connectable to the horizontal element of the vertical frame, whereby the said plurality of cells, when connected to said horizontal element, hang therefrom.

4. A method according to claim 2, wherein the perimeter of the horizontal cross-section of each cell is comprised between 5 cm and 100 cm.

5. A method according to claim 2, wherein the height of each cell is comprised between 100 cm and 250 cm.

6. A method according to claim 1, wherein the distance between two adjacent cells is 100 mm or less.

7. A method according to claim 6, wherein each cell is separately connected to the vertical support means.

8. A method according to claim 6, wherein all cells are connected to form a single body.

9. A method according to claim 8, wherein the plurality of cells is created in two layers of weldable material by welding the two layers vertically at intervals.

10. A method according to claim 1, wherein each two adjacent cells are connected by at least one point.

11. A method according to claim 1, wherein said at least one gas inlet comprises a dip pipe for air, the diameter of the said dip pipe being sufficient to permit the flow of an amount of air which efficiently mixes the biomass within each cell.

12. A method according to claim 1, further comprising cooling means to cool the biomass contained within each cell, when a predetermined temperature is exceeded.

13. A method according to claim 12, wherein the cooling means comprise water sprinkling means for sprinkling water along each cell.

14. A method according to claim 1, wherein the cells are made of weldable material.

15. A method according to claim 14, wherein the weldable material is polyethylene.

16. A method according to claim 1, further comprising passages which interconnect between adjacent cells.

17. A method according to claim 1, wherein the bottom portion of each cell is conical in shape, thereby promoting fluidization and mixing and preventing sedimentation of the biomass.

18. A method of producing β-carotene from β-carotene-producing microalgae, comprising the steps of:

A) providing a growth apparatus, comprising in combination:

a) a plurality of vertical elongated transparent flexible cells, capable of containing a microalgae biomass;

b) vertical support means to support the plurality of cells in close juxtaposition to one another, and in vertical position;

c) at least one gas inlet and one gas outlet, to permit the bubbling of gas through the biomass in each cell and the ventilation of each cell;

d) at least one cell fluid inlet and/or fluid outlet, to permit feeding of nutrient solution to the biomass and harvesting of the biomass from each cell; and e) central conveying means connected to each said at least one cell fluid inlet and/or fluid outlet to receive and convey biomass harvested from the plurality of cells, all or part of them, away from the growth apparatus;

B) filling the cells growth apparatus through said at least one cell fluid inlet and/or fluid outlet with a nutrient solution containing biomass of carotene producing microalgae to be grown;

C) bubbling through said at least one gas inlet of the cell filled with nutrient solution, air in an amount sufficient to obtain efficient mixing of the biomass and removal of oxygen therefrom through said at least one gas outlet;

D) providing to the growth apparatus cell contained biomass, $CO_2$ in an amount sufficient to promote biomass growth;

E) periodically harvesting from the cell of the growth apparatus, the biomass grown by removing a fraction of the volume contained in each cell through said common conveying means, causing solids contained therein to precipitate and recycling the solution from which the solids have precipitated to the cells through said at least one fluid inlet and/or fluid outlet;

F) making-up the fraction removed from the cells with nutrient solution and/or materials as required; and G) recovering β-carotene from the harvested biomass.

19. A method according to claim 18, wherein the make-up nutrient solution of step F consists at least partially of recycled nutrient solution from the biomass separation step.

20. A method according to claim 18, wherein $CO_2$ is provided together with the air.

21. A method according to claim 20, wherein the content of $CO_2$ in the air is about 2–3%.

22. A method according to claim 18, wherein the microalgae is *Dunaliella sp.*

* * * * *